United States Patent [19]

Andries

[11] Patent Number: 4,991,581
[45] Date of Patent: Feb. 12, 1991

[54] ACOUSTIC PROCESSING APPARATUS

[75] Inventor: Francis M. Andries, Austin, Tex.

[73] Assignee: Andries Tek R&D Limited Partnership, Austin, Tex.

[21] Appl. No.: 164,204

[22] Filed: Mar. 4, 1988

[51] Int. Cl.⁵ .......................... A61B 5/02; A61B 7/00
[52] U.S. Cl. ..................................... 128/715; 128/773
[58] Field of Search ................ 128/773, 715; 381/169, 381/173, 205

[56]  References Cited

U.S. PATENT DOCUMENTS

| | | | |
|---|---|---|---|
| 3,160,708 | 12/1964 | Andries et al. | 128/715 X |
| 3,790,712 | 2/1974 | Andries . | |
| 4,226,248 | 10/1980 | Manoli | 128/773 |
| 4,428,381 | 1/1984 | Hepp | 128/773 X |
| 4,672,977 | 6/1987 | Kroll | 128/773 X |
| 4,679,570 | 7/1987 | Lund et al. | 128/715 |
| 4,712,565 | 12/1987 | Katz et al. | 128/715 |
| 4,792,145 | 12/1988 | Eisenberg et al. | 128/715 |

OTHER PUBLICATIONS

Chu et al.; "A Noninvasive Electroacoustical Evaluation Technique of Cartilage Damage in Pathological Knee Joints"; *Med and Biol. Eng. and Comput* 1978, 16, pp. 437-442.

Siemens' brochure "Mingograf 7".
Siemens' brochure "Heart sound Amplifier 858".

*Primary Examiner*—Max Hindenburg
*Assistant Examiner*—John P. Lacyk
*Attorney, Agent, or Firm*—Arnold, White & Durkee

[57]  ABSTRACT

An apparatus and method of recording and processing acoustics, such as body sounds, for assessment of the sound and possible diagnosis of any abnormalities associated with the sound. The apparatus includes an electronic stethoscope for acoustic pick-up and a convertor section for converting the acoustic analog signal into a digital signal. The operator can track the acoustic signal on an acoustic headset. The digital signal is continuously stored in computer memory and the operator can selectably retain a portion of the digital signal in volatile memory. The apparatus further includes a signal editing function for selectably altering the retained digital signal to isolate the waveform of interest. To this end, the retained signal is fed through the conversion section for conversion to an output analog signal for display on the monitor and play on the acoustic headset. The retained signal can be further edited as desired and stored in nonvolatile memory. The edited waveform is not only useful in diagnosing abnormalities but is also easily preserved for historical interest.

30 Claims, 3 Drawing Sheets

ACOUSTIC PROCESSING APPARATUS

BACKGROUND OF THE INVENTION

1. Field of the Invention

This invention relates to an apparatus and method for recording and processing acoustic signals for use in assessing the condition of the acoustic source. In particular, the method and apparatus is particularly adapted for detecting and recording body sounds, and editing and visually displaying the body sounds for diagnosis and historical tracking.

2. Description of the Related Art

Detecting abnormal sounds is a useful method for diagnosing an abnormal condition in the source of the sound. For example, bearings, engines or other mechanical components often emit abnormal sounds long prior to failure, and detection of such abnormal sounds can be useful in predicting impending failure. While the use of sounds as a diagnostic or assessment method is undoubtedly useful, in practice it is sometimes difficult and limited. Difficulties arise because most sounds of interest occur over a very wide frequency range making detection and analysis difficult. Further, most sounds of interest occur simultaneously with a large number of other, extraneous sounds, making isolation of the acoustic of interest difficult.

Perhaps the most widespread use of monitoring sounds for predicting the condition of the sound source is the use by physicians of the acoustic stethoscope to listen to body sounds. The acoustic stethoscope is a good example of the usefulness and difficulty of using sounds as a diagnostic or assessment method. The acoustic stethoscope has been in use since the early 1800's, and is currently used twice as much as all other diagnostic procedures combined. In addition to widespread use, it has been found that a qualified cardiologist with a stethoscope forms his diagnostic conclusions based on physical examination, auscultation, and patient history, and that this initial conclusion is rarely (less than 6%) altered by secondary testing.

While auscultation is the most widely used method of diagnosis, many problems exist. First, many organ sounds or sounds within organs lie at the edge of human perception due to faint intensity, low or high frequency, high speed, proximity to other sounds, or overall complexity. Second, auscultation is a skill which is difficult to teach, develop, and maintain. Even if a physician can isolate a body sound of interest, a physician must rely solely upon the physician's experience and memory—remembering abnormal sounds is a difficult problem under the best of circumstances. It is not surprising that in testing, a large number of practicing physicians fail basic auscultatory testing using conventional acoustic stethoscopes.

A partial solution to some of the problems associated with conventional acoustic stethoscopes is the electronic stethoscope. U.S. Pat. Nos. 3,160,708 and 3,790,712 (incorporated herein by reference) illustrate such electronic stethoscopes. Electronic stethoscopes in part overcome limitations of the human hearing system by providing a transducer pick-up of the acoustic which is far more sensitive to frequency and amplitude than the human ear. Such electronic stethoscopes also amplify even faint sounds extending the detection range of the human ear.

Notwithstanding their advantages, electronic stethoscopes do not provide a method for recording a patient's body sounds, isolating a particular sound, or displaying the body sounds so that the sound can be heard and also visualized to enhance perception and analysis. It would be a significant advance in the art if a method and apparatus were devised which could electronically detect sound and record, store, edit, and display such sounds for diagnosis and further study. Such accumulation of data would not only aid in assessment and diagnosis, but would also provide an educational medium where auscultatory skills could be improved and maintained and a data base for comparison purposes.

SUMMARY OF THE INVENTION

The present invention solves many of the problems associated with conventional auscultation outlined above by providing an apparatus and method which detects and records complex sounds and provides for editing, storing and visualization of such acoustic signals. As such, the present invention is a significant aid in using auscultation as a diagnostic tool, particularly in medical applications where body sounds are often complex, and intermingled with other sounds.

Broadly speaking, the apparatus of the present invention provides a transducer for detecting the sound and for producing an input analog signal representative of the sound. The input analog signal is processed by a convertor section which converts the analog signal to an input digital signal. The input digital signal is processed by an editor section which includes a computer for storing in memory at least a portion of the input digital signal. A recorder (e.g. non-volatile memory) is coupled to the computer for selectably recording the digital signal stored in the computer's memory. The convertor is also operable for converting the edited digital signal to an edited analog signal which is communicated to the operator at an interface, such as a display monitor. The apparatus is preferably multi-channel for detecting, processing, and displaying more than one sound at a time.

Preferably, the interface includes both a display monitor and a stethoscope headset for visually and aurally analyzing the edited analog signal. If desired, the operator can place the apparatus in a mode for visually and aurally tracking the input analog signal (raw data). Preferably the input analog signal is continuously digitized and stored in computer memory, so that when the operator observes a waveform of interest, he can command the computer to capture a portion of the signal he has observed (e.g. the last four seconds of the signal). With the signal captured in memory, the operator can edit the signal of interest, replay the signal through the interface, or store an edited version of the signal.

The recording mechanism preferably comprises non-volatile memory, such as floppy or optical disk, and is useful in making a permanent record of the edited signal of interest. The apparatus can play back from the recorder a signal on one channel, while it detects and displays a second signal on a second channel. Thus, the operator can detect and edit a sound while comparing such a signal with a signal from its database.

An alternative embodiment envisions a playback, or teaching system, in which digital storage is coupled to an editing and convertor section. The convertor section converts the stored digital signal, permits editing of the stored digital signal, and converts the digital signal to an analog signal for display to the operator or students.

DETAILED DESCRIPTION OF THE PREFERRED EMBODIMENTS

Figure 1:
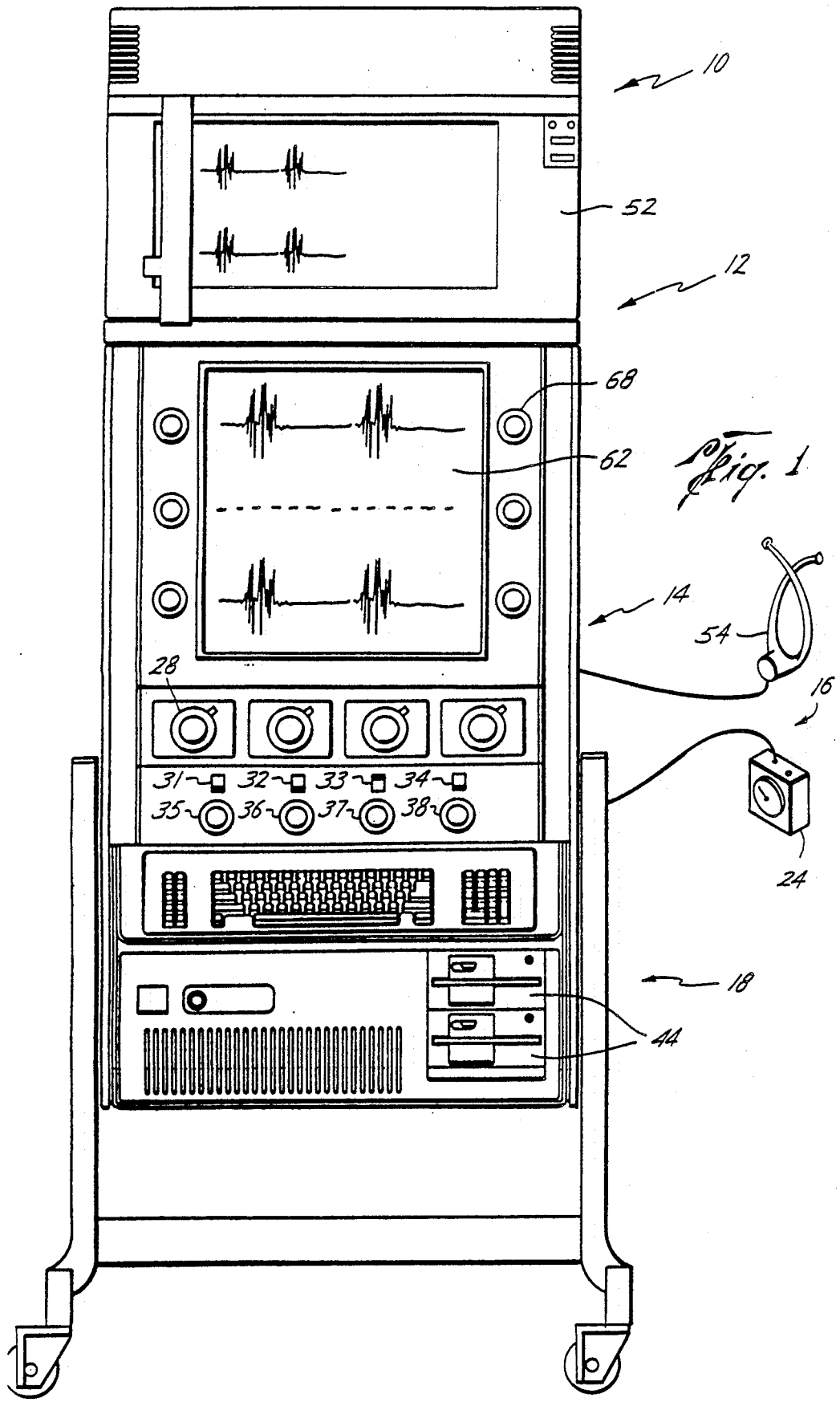
FIG. 1 is an elevational view of the apparatus of the present invention.

Turning now to the drawings, an acoustic pick-up and processing apparatus 10 in accordance with the present invention is illustrated. Broadly speaking, the apparatus 10 includes an interface section 12, and editing section 14, transducer means 16, and a recorder mechanism 18 (top to bottom in FIG. 1). A convertor circuit 20 is disposed within the housing of the editing section 14 and is illustrated in some detail in FIG. 3.

Broadly speaking, the apparatus 10 is designed for the pick-up and recording of acoustic signals, such as body sounds, where the sound might be useful in predicting the condition of the sound source or an early indication of failure of the sound source. The transducer means 16 is configured for detecting the sound and for producing an input analog signal representative of the sound. The convertor circuit 20 receives this input analog signal from the transducer 16 and converts the input analog signal to an input digital signal. The editing section 14 is coupled to the convertor circuit 20 for receiving and editing this input digital signal, and includes a computer 22 which stores at least a portion of this digital signal in memory computer 22. The recorder section 18 is coupled to the computer 22 for selectively recording the digital signal stored in memory. The convertor circuit 20 receives the edited digital signal from the editing section 14 and converts the edited digital signal to an edited analog signal. This edited analog signal is fed to the interface section 12 which communicates the edited analog signal to the operator.

Figure 3:
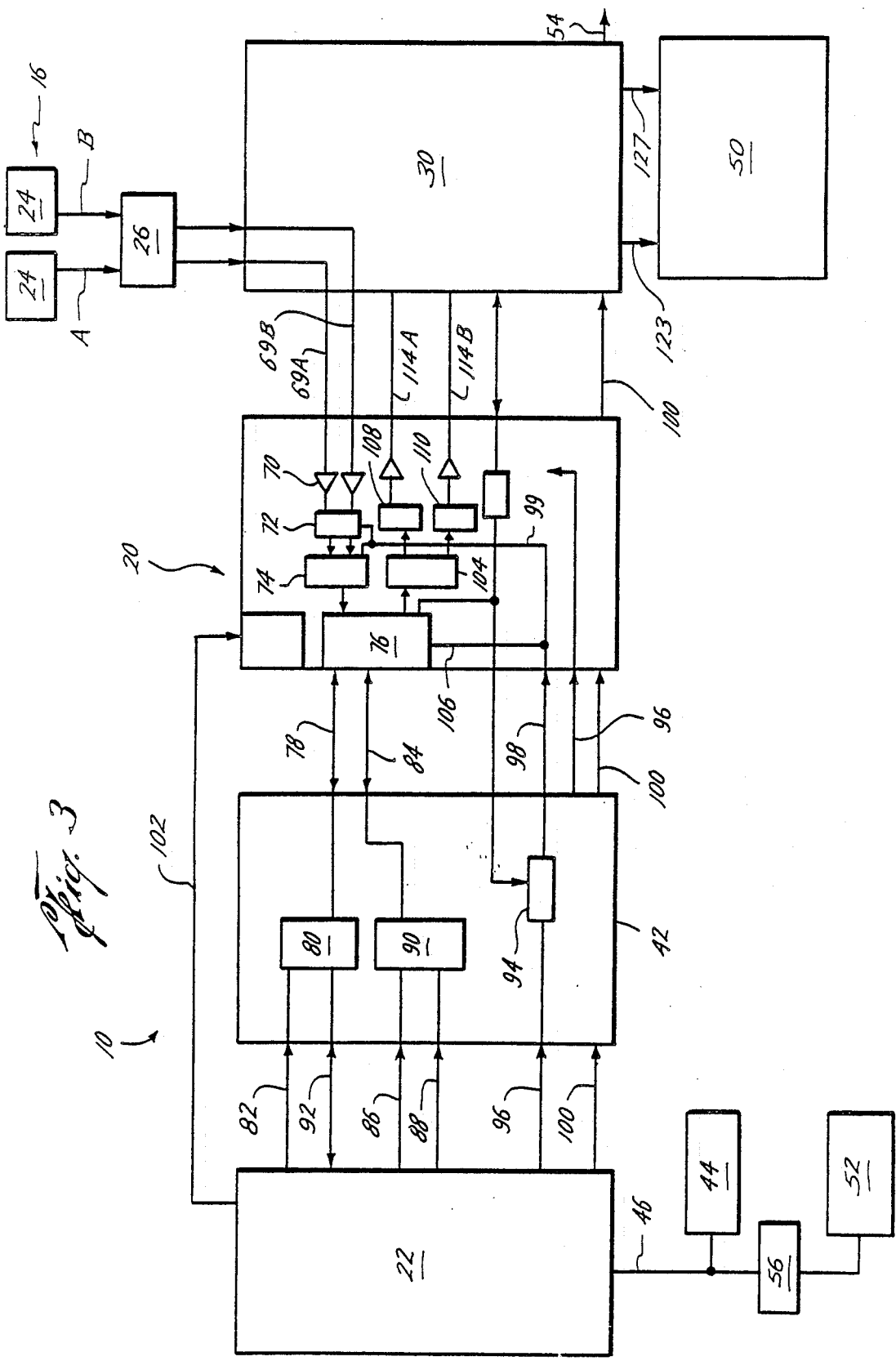
FIG. 3 is a circuit block diagram of the present invention.

In more detail, the transducer means 16 comprises two electronic stethoscope pick-up sections 24 (only one being illustrated in FIG. 1). Such electronic stethoscopes are known in the art and are described in U.S. Pat. Nos. 3,160,708 and 3,790,712 (incorporated herein by reference). As shown in FIG. 3, several pick-up sections 24 can be utilized, depending upon the number of processing channels available in the apparatus 10. In the embodiment of FIG. 3, two channels (A and B) are provided. While in some situations it might be desirable to filter or condition the analog signals coming from the pick-ups 24, such noise reduction techniques often result in signal damage. In the preferred embodiment of FIG. 3, the analog signals are fed directly to input amplifiers 26. As shown in FIG. 1, amplifier controls 28 are provided to control the amplifier gain. Although four amplifier gain controls are illustrated in FIG. 1 for four channel operation, only two channels are utilized in the embodiment illustrated.

Control panel 30 is disposed below the amplifier controls 28 as shown in FIG. 1. The control panel 30 includes eight editing controls, four of which (controls 31-34) are two position toggle switches, while the other four are rotary dial switches (controls 35-38). "Channel select" control 31 is a two position toggle which allows the operator to switch between the two input channels A and B. The "monitor display" switch 32 allows the operator to select for display either raw data directly from one of the input amps 26 or the display of a processed signal ("processed" meaning the signal has been digitized and stored in memory, and converted to analog for display). "Enter" control 33 allows the operator to selectively enter or capture a signal into computer memory, while "menu" control 34 simply calls up the computer menu. Rotary control 35-38 includes headset volume 35, pause 36, cursor position 37, and cursor length 38.

The computer 22 illustrated in the drawings is a Commodore 128 and includes keyboard 40 (FIG. 1) and an input/output board 42 (FIG. 3) in the expansion slot of the Commodore 128. The recorder section 18 includes two disk drives 44 which are connected to the computer through a serial daisy chain 46 interface as shown in FIG. 3.

The interface section 12 in the preferred embodiment includes a monitor section 50, x-y plotter 52, and an acoustic headset 54 as shown in FIG. 1. As shown in FIG. 3, the plotter 52 is connected to the computer 22 through a serial interface 56. The headset 54 is similar to those provided as a component of electronic stethoscope and is selectable to monitor either the raw data input analog signals from the transducer means 16 or monitor the processed signal.

The monitor section 50 is somewhat complex in that conventional magnetic deflection x-y oscilloscopes cannot be slewed fast enough to display two or more channels on the scope screen. Broadly speaking, the monitor section 50 includes a scope broad 60 (FIG. 4), a scope 62, isolation board 64 and monitor board 66. The scope 62 is a magnetic deflection oscilloscope, but uses the conventional horizontal axis for its vertical axis, and the normal vertical axis for its horizontal axis. Thus, the raster sweep is in the vertical. The scope board 60 controls the video raster scope 62 to give a frequency response to 1,000 Hertz with practically no limitation on the number of channels displayed. The scope controls 68 are provided (FIG. 1) to alter the display of the scope 62 and includes the following controls: brightness, sweep select, sweep per second, channel A position, channel B position, and tic position.

Turning now to FIG. 3, the circuitry of the apparatus 10 is broadly illustrated in block diagram form. As can be appreciated, the analog signals A and B produced by pick-ups 24 are amplified at the input amplifier section 26, and the amplified input analog signals 69A and 69B as supplied to the control panel 30. From a comparison of FIGS. 1 and 3, it will be appreciated that the gain control knobs on amplifier panel 28 control the operation of the direct amplifiers 26. The amplified input analog signals 69A/B are fed to the monitor display control 32 of the control panel 30. Both amplified input analog signals 69A and 69B are fed to convertor circuit 20 and also the monitor display control 32. The channel select switch 31 is interconnected to the monitor control 32 to determine which input analog signal is supplied to the headset. That is, the channel select switch 31 will determine which channel A or B is supplied to the headset. Additionally, the headset volume control knob 35 is connected to the channel select switch 31 to feed and control the strength of the signal selected to the headset 54. The monitor display control 32 taps a header so that the monitor switch 32 determines whether an amplified input analog signal (i.e. raw data)

will be heard in headset 54, or whether a processed signal (from the header) will be heard in headset 54. Thus, by use of the monitor switch 32 and channel select switch 31, the signal to the headset 54 can be determined.

As shown in FIG. 3, the analog input signals 69A and 69B are supplied to conditioners 70 of the convertor circuit 20. The analog signals 69A/B are conditioned (i.e. amplified, filtered, offset/gain) and fed through the multiplex/sample-hold 72 to the analog-to-digital convertor 74. Latch 76 clocks out eight data and six strobes to the octal bus transceiver 80 of I/O board 42, via data line 78 and strobe line 84.

As can be appreciated, the I/O board 42 provides the interface between the computer bus of the computer 22 and the convertor circuit board 20 (and also certain hardware timing). CPU in the Commodore 128 is a Motorola 8510 having a memory-mapped input/output and two I/O space strobes. Thus, space strobe 86 can be used with A0–A7 information 88 through address-/decode 90 to select a particular address on latch 76. The octal bus transceiver 80 buffers the data bus 92 with read/write line 82 controlling the direction.

Phase 2 clock, 1.02 Mhz, drives counter 94 through line 96. Counter 94 divides the clock signal to about 8 khz and 4 khz (line 98), and as can be seen from FIG. 3 the 8 khz signal starts a conversion on the A to D board 74 (line 99) while the 4 khz signal clocks data to the D/A convertors (line 106).

The convertor circuit 20 receives its +5 volt digital power supply from the computer 22 via the I/O board 42 as shown by line 100. The 9 volt AC power supply is fed directly from a user port on the computer 22 to the convertor circuit 20 as shown by line 102.

Looking at the flow of information from the computer 22 through the convertor circuit 20, 24 bits of D/A information plus four bits of control information are clocked out to latches 76. Latches 76 drive deglitching latches 104, which are clocked by the 4 khz strobe (line 106). The deglitching latches 104 prevent glitches between the writing of the low nibble and the high bite when converting digital to analog. All 24 bits of digital information are in place by the time the deglitching latches 104 are clocked. The four control bits are: MODE, which controls scope mode (alphanumeric or trace); SYNC, which triggers a sweep in the scope; trigger for the two CURSOR one-shots; and a trigger for the PAUSE one-shot. The digital information from the deglitching latches 104 are clocked out to the digital-to-analog convertors 108, 110 and through filters 112 as shown in FIG. 3. The output at 114A and 114B represents the processed analog output fed to the control panel 30. The monitor section 50 receives signals from the panel 30 for display.

Figure 4:
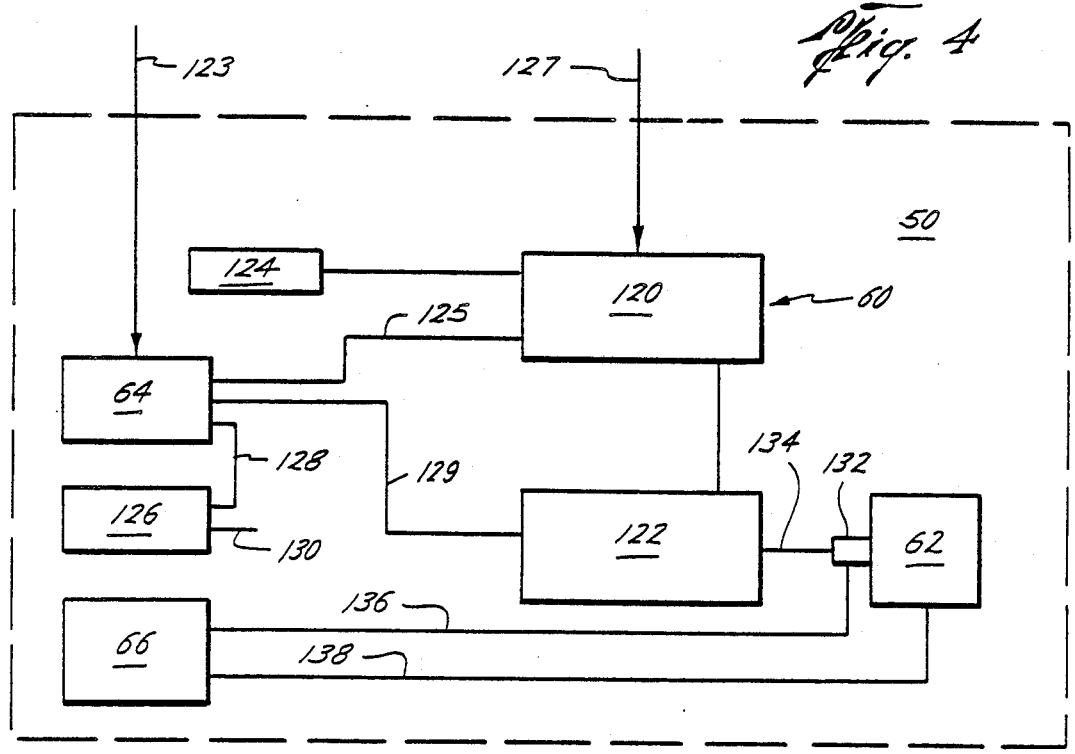
FIG. 4 is a circuit block diagram of the scope board and monitor used in the apparatus of the present invention.

With reference to FIG. 4, the monitor section 50 is illustrated in more detail in block diagram form. The scope board 60 includes a logic section 120 and sweep section 122 for driving the scope 62. In FIG. 4, block 124 represents a circuit for the addition of more than two channels for scope display, which is not used in the illustrated embodiment. Line 123 in FIG. 4 represents the analog inputs 69A and 69B from the header of the control panel 30 to the isolation board 64. Line 125 represents the analog inputs from the isolation board 64 to the logic section 120. Isolation board 64 simply isolates the channel signals to prevent interference. Line 127 represents the processed analog outputs 114A/B fed through the control panel 30 to the logic section 120.

The power supply block 126 generally illustrates that +15 volt, −15 volt, and analog ground are supplied through analog power supply line 128 to isolation board 64. The +5, −5 volt analog supply for scope board 60 is taken from the +15 volt, −15 volt supply, and consists of a series pass circuit with an IC voltage reference and op-amp driven tracking regulators. The scope board power is fed through line 129 to the two sweep ramp generators of the sweep section 122 up to power output stage. The isolation board 64 has a two stage regulator powered from this +15, −15 volt supply power via line 128, to stiffen the supply voltages at the reference ramp generator of sweep section 122. The line 130 represents +5 volt and digital ground, with it being understood that a separate ground is used for the digital and analog sections.

As previously mentioned, the scope 62, it should be remembered that the raster scan scope 62 is turned 90° so that the raster sweep appears in the vertical on the scope 62 (compare FIG. 1). Therefore, sweep section 122 drives the horizontal sweep 134 of yoke 132 while the vertical scan is controlled from the monitor board 66 through line 136. The monitor board 66 also provides the hv filament control 138. Between sweeps the beam of the scope 62 is allowed to rest at zero horizontal deflection angle.

SOFTWARE

The software which drives the computer 22 consists of two major parts: (1) the menu and keyboard handling routines which are written in BASIC; and (2) the acquisition display routines which are written in assembly code. Appendix I is a printout of the BASIC source code and assembly code programming of the preferred embodiment of computer 22.

the menu and keyboard handling routines simply prompt the operator with his options and await the operator responses. That is, the apparatus 10 is designed to be "menu driven." Because the scope 62 is rotated 90°, the menu routines employ an altered character set for coping with this modified screen orientation.

The assembly code routines handle the flow of digital data to and from the A to D convertors 74 and D to A convertors 108, 110 and sends control to the scope board 60. Because a hardware clock dictates sampling and conversion rates, the assembly code does not have to account for such timing. The assembly code routines do control where data is stored and what data is sent to the D/A convertors 108, 110, scope board 60, and RAM memory in the computer 22. The assembly codes also control disk access and storage to disk drive 44 by calling I/O routines resident in ROM in computer 22.

OPERATION

Operation of the apparatus 10 allows the operator to acquire data while the operator is seeing and hearing the same data. When the operator sees or hears data of interest, the operator can capture the data in memory and edit the signal. The transducer means 16 is coupled to the acoustic of interest, and while the apparatus 10 was specifically designed for the pick-up and processing of body sounds, it should be appreciated that other acoustics can be processed as well. For example, the transducer 16 could be placed for pick-up of engine bearing noise and the acoustic signals analyzed for prediction of uneven wear, fatigue, or even eminent failure.

Whether the acoustic of interest is a body sound, machine sound, or some other type of sound, the apparatus 10 is configured for handling data from DC to 1200 Hertz. It is not uncommon for many acoustics to have signals in the thousand Hertz range.

While body sounds are commonly used as a diagnosis technique, such sounds are often difficult to pick up and analyze. Physiological acoustic data include lung, heart, gastrointestinal, korotkoff, bruits, and joint crepitations. As shown in FIG. 3, the illustrated apparatus 10 includes two pick-ups 24 for acquiring two acoustics simultaneously. It should be appreciated that while two channels are illustrated, more channels could be added. The use of multiple data acquisitions channels allows two different areas to be probed simultaneously. For example, the two pick-ups 24 can be placed for two views of the heart, to acquire simultaneously two separate channels of heart sounds. The two channels can be displayed simultaneously and the two channels reconciled. It is also possible to supply another type of analog signal on a second channel—e.g. electrocardiogram signal—for comparison to the acoustic signal on the first channel. In a preferred form, a body sound is detected, processed, and displayed on a first channel, while a comparison body sound is retrieved from disc drive 44 and displayed on the second channel.

On power up, the following main menu appears on the scope 62:

MAIN MENU
1. ACQUIRE WAVEFORM
2. SHORTEN WAVEFORM
3. BLANK PARTS OF A WAVEFORM
4. INSERT PAUSES
5. DISPLAY WAVEFORM
6. SWAP WAVEFORMS
7. FREQUENCY ANALYSIS
8. PLOT WAVEFORM
9. DISK UTILITY MENU

With two pick-ups 24 in place, the operator will normally select the "ACQUIRE WAVEFORM" option. In this option, the A and B analog signals are fed through the pick-ups 24 to the input amplifiers 26. The gain on the amplifiers can be adjusted using the A and B channel amplifier control knobs 28. Normally, the operator at this time will set the scope controls 68, i.e. sweep speed, position, brightness, and tic position for a time reference. The operator has the option of listening to either A or B channel using the channel select control 31 and monitoring either the raw data analog input or processed signal using the monitor switch 32.

Regardless of whether the operator is monitoring the raw data or processed signal, the amplified input analog signals 69A/B are sent to the 12 bit A to D convertors 74. As can be appreciated from FIG. 3, the amplified input analog signals 69A/B are continuously digitized and stored in memory in computer 22 and reprocessed through convertor circuit 20 to produce analog outputs 114A/114B. The operator can thus switch back and forth using the monitor switch 32 between raw data amplified input analog signals 69A/69B and processed signals 114A/114B. Therefore, the operator can be certain that good data is continuously flowing into and out of memory in the computer 22.

When the operator detects a waveform of interest, the Enter switch 33 is toggled to capture the last four seconds of information in memory. It can be appreciated that additional memory in the computer 22 will allow the capture of additional time; the embodiment of computer 22 illustrated having sufficient memory to capture approximately four seconds of information. With a waveform of interest captured in memory, the operator presses the menu control 34 to return to the main menu. The operator can, of course, select any of the main menu listed options in any desired order.

The "SHORTEN WAVEFORM" option allows blanking of one or both waveforms captured in memory. In this mode, the cursor position control 37 operates to set the beginning of the captured waveform, while the cursor length control 38 sets the length. Controls 37, 38 are thus set to blank out the beginning and end of the captured waveform as desired. During this procedure, the captured waveform is being continuously displayed on scope 62 and can be heard through headset 54. When the desired start and end of the waveform is set, the operator may again press the Enter switch 33 substituting this edited waveform in memory. The edited waveform can now be monitored on scope 62 and headset 54. With the one or two waveforms edited for length, the operator can press the Menu button 34 and return to the main menu.

The "BLANK PARTS OF WAVEFORM" option allows for blanking out different parts of the waveform. Many acoustic signals, particularly heart sounds, come in complex arrangements that are difficult to hear and distinguish. This option allows unwanted areas of the waveform to be blanked out so that only the waveform of interest is left. In this option, the cursor controls 37, 38 are used to describe a window that is to be blanked out. Each time a portion of the waveform is blanked out, the Enter button 33 is depressed to capture the new edited waveform. Until the Enter button 33 is depressed, the original unblanked waveform is retained in memory.

The "INSERT PAUSE" option is particularly desirable where the acoustic signals of interest have fast repetition rates. Such fast repetition rates may make it difficult to hear and visualize specific elements within a single cycle. A pause inserted between the different elements can slow the acoustic signals so that the signals can be heard and visualized and all elements within a cycle discerned. In the "INSERT PAUSE" mode the Cursor Position Knob 37 is set wherever in the waveform the pause is desired, and the Enter button 33 is depressed to insert the pause. The Pause Control Knob 36 is used to vary the length of the pause. If it is desired to start over, the operator can hold down the Enter button 33 while selecting "INSERT PAUSE" from the main menu. The start over function erases all pauses previously inserted without losing the original waveform information.

The "DISPLAY WAVEFORM" mode simply displays whatever information is in channel A and channel B memory. Usually the operator will retain the two unedited waveforms in memory, so that in this mode the two unedited waveforms will be displayed without pauses or blanks.

The "SWAP WAVEFORM" mode allows the A and B channel waveforms to be switched. The operator may want to invert the A and B channels to apply the zero crossing test to the desired waveform (can only be applied to channel A). Additionally, the apparatus 10 is configured to save only the waveform from channel A on disk. Therefore, if it is desired to save the channel B waveform, the operator will swap waveforms prior to saving the waveform on disk.

The "FREQUENCY ANALYSIS" mode performs a zero-crossing frequency analysis on the waveform of channel A. The results appear as a graph on channel B, consequently the memory contents of channel B are destroyed. Therefore it is important to save the channel B waveform either on disk or hard copy (if desired) prior to such a frequency analysis.

The "PLOT WAVEFORM" option simply plots the A and B memory contents to the x-y plotter 52.

The "DISK UTILITY MENU" performs the following functions:

DISK DIRECTORY
FORMAT NEW DISK
BACKUP DISK
SAVE WAVEFORM
LOAD WAVEFORM
ERASE WAVEFORM
VALIDATE FILE
DISK ERROR STATUS
RETURN TO MAIN MENU

The "DISK DIRECTORY" function loads and manipulates the disk directory data for display on the scope 62. The operator may hit any key but "Q" to advance to the next screen. Once the operator locates the item of interest, pressing "Q" aborts the process and returns to the disk menu.

The "FORMAT NEW DISK" utility is provided to prepare a new disk inserted in a drive 44 to receive data, e.g. waveforms.

The "BACKUP DISK" function is provided, which of course makes a backup to one of the drives 44.

The "SAVE WAVEFORM" function saves whatever waveform is in channel A. This function also asks that the saved waveform be named for later location.

The "LOAD WAVEFORM" function asks for the name of the waveform to be loaded, locates it on disk, and loads it into channel A. The previous contents of channel A are moved to channel 2 and the contents of channel 2 discarded.

The "ERASE WAVEFORM" function asks for the name of the disk file to be erased, while the "VALIDATE FILE" function cleans up the disk throwing out garbled files.

The "DISK ERROR STATUS" function is provided to check the disk, while the final utility is simply a "RETURN TO MAIN MENU" function.

EXAMPLE

Figure 2:
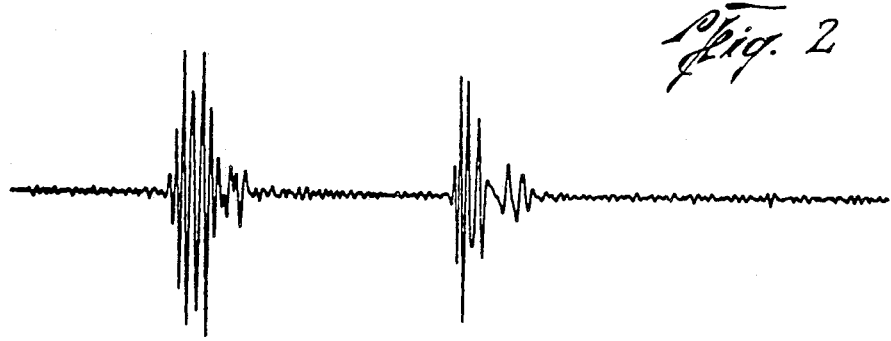
FIG. 2 is a display of a two channel output of the apparatus of the present invention.

Turning now to FIG. 2 the two channel display is illustrated. The top channel or A channel represents an edited display of a normal heart valve. The bottom or B channel represents an abnormal heart valve with harsh systolic election murmur. The physician is using a single pick-up 24 to track and process the harsh systolic murmur on channel B in near rear time. The channel A display represents a normal heart valve recalled from disk memory. Comparison of the A and B channels reveals the difference.

FIG. 2 illustrates a first plot routine in which the ordinate represents the intensity range while the abscissa represents 10 milliseconds per division. A second plot routine is available which plots frequency at crossover (from 10 to 1000 Hz) on the ordinate versus time on the abscissa. If desired, both the first and second plots can be displayed simultaneously, to show the operator frequency and amplitude over time.

ALTERNATIVE EMBODIMENT

An alternative embodiment of the present invention is nearly identical to the preferred embodiment illustrated in the drawing, but is useful only as a teaching system. That is, the alternative embodiment is a playback only system, without any signal acquisition ability.

In the alternative embodiment playback system, a digital recording, such as the disk drive 44, is used to store a database of the acoustics of interest, e.g. heart sounds. Other digital or recording media can easily be used such as ROM, non-volatile RAM, or preferably optical disk drives with their enhanced storage capabilities. With the data base of digitally recorded sounds, selected sounds (selected by file name) can be played back through a system in a manner similar to FIG. 3. That is, the recorded sounds are played through the digital-to-analog conversion section of the convertor circuit 20 for display on the scope 62 and communication to the headset 54. Multiple headsets are provided for accommodating several students at a time. During the playback, the signals can be edited for display, although preferably the waveforms stored in the disk drives 44 cannot be altered. Such a playback system is particularly effective in teaching students auscultation skills and enhancing and monitoring such skills.

What is claimed is:

1. An apparatus for pick-up and recording of acoustic signals, such as body sounds or the like, comprising:
   transducer means for detecting sound and for producing an input analog signal representative of the sound;
   convertor means for receiving the input analog signal from the transducer means and converting the input analog signal to a digital signal;
   editing means coupled to the convertor means for receiving the digital signal and for editing the signal, including
     means for adjusting the waveform of the digital signal, and
     computer means for storing in memory at least a portion of the digital signal;
   recorder means coupled to the computer means for selectably recording at least a portion of the digital signal;
   the convertor means being operable for receiving the digital signal from the memory of the computer means and for converting the digital signal to an output analog signal; and
   interface means coupled to the convertor means for receiving the output analog signal and adapted for communicating the output analog signal to the operator.

2. The apparatus according to claim 1, the interface means being selectably couplable to the transducer means and selectably operable for communicating the input analog signal to the operator.

3. The apparatus according to claim 1, the interface means including a headset for aural representation of an analog signal.

4. The apparatus according to claim 1, the interface means including a plotter for visual representation of an analog signal.

5. The apparatus according to claim 1, the interface means including a monitor for visual representation of an analog signal.

6. The apparatus according to claim 5, the monitor comprising a raster scan monitor in which the raster sweep is oriented in the vertical axis.

7. The apparatus according to claim 6, the monitor being operable for displaying a plurality of signals simultaneously.

8. The apparatus according to claim 1, the transducer means including a plurality of pick-up devices and the convertor means operable for receiving and converting a plurality of signals simultaneously.

9. The apparatus according to claim 1, the computer means being operable for retaining an operator designated waveform of the digital signal in memory.

10. The apparatus according to claim 9, the editing means including a plurality of editing controls and circuits for editing the retained digital signal.

11. The apparatus according to claim 10, the editing controls including a cursor position control for setting the cursor beginning of the retained digital signal.

12. The apparatus according to claim 10, the editing controls including a cursor length control for setting the duration of the retained digital signal.

13. The apparatus according to claim 9, the computer means including volatile memory and non-volatile memory, the designated waveform being retained in volatile memory and the computer means being operable for storing the designated waveform in non-volatile memory.

14. The apparatus according to claim 13, the non-volatile memory comprising a magnetic disc drive.

15. The apparatus according to claim 9, the editing means including a plurality of editing controls and circuits operable for editing the designated waveform, the computer means being operable for replacing the designated waveform with the edited waveform in memory.

16. The apparatus according to claim 10, the adjusting means including controls to blank out areas of the waveform of the retained digital signal.

17. The apparatus according to claim 10, the adjusting means including controls for inserting a pause into the waveform of the retained digital signal.

18. A method of acquiring and processing a sound for assessing a condition, diagnosing a problem, or the like, comprising the steps of:
picking up the sound with a transducer and producing an input analog signal representative of the sound;
converting the input analog signal to a digital signal;
storing at least a portion of the digital signal in computer memory;
converting said portion to an output analog signal;
displaying the output analog signal; and
editing said digital signal portion by adjusting the waveform to produce an edited waveform for assessment.

19. The method according to claim 18, including the steps of:
converting said edited waveform to an edited analog signal; and
displaying said edited analog signal.

20. The method according to claim 18, including the step of storing said edited waveform in non-volatile memory.

21. The method according to claim 18, including the steps of:
retrieving a second digital signal from memory;
converting the second digital signal to a second analog signal; and
simultaneously displaying the output and second analog signals.

22. The method according to claim 18, including the steps of:
retrieving a second digital signal from memory;
converting the second digital signal to a second analog signal; and
displaying simultaneously the edited waveform and second analog signal.

23. The method according to claim 18, including the step of aurally monitoring the input analog signal.

24. The method according to claim 18, including the step of aurally monitoring the output analog signal.

25. The method according to claim 18, including the steps of:
picking up a plurality of sounds simultaneously and producing a plurality of input analog signals;
converting the plurality of input analog signals to a plurality of digital signals;
storing at least a portion of each digital signal;
converting at least two of said stored digital signals to output analog signals; and
displaying simultaneously the two or more output analog signals.

26. An apparatus for visually displaying one or more stored waveforms comprising:
non-volatile storage means for storing a plurality of digital signals each representative of an acoustic waveform;
computer means coupled to the non-volatile storage means for retrieving a waveform from nonvolatile storage;
editing means coupled to the computer means for adjusting the retrieved waveform to produce an edited retrieved waveform;
convertor means coupled to the computer means and operable for converting the edited retrieved digital waveform to an analog signal representative of the edited retrieved waveform; and
video display means coupled to the convertor means for receiving the analog signal and visually displaying the analog signal.

27. The apparatus according to claim 26, the display means comprising a raster scanned scope in which the raster sweeps in the vertical.

28. The apparatus according to claim 26, the computer means, convertor means, and display means being operable to simultaneously retrieve and display a plurality of waveforms.

29. An apparatus for pick-up and recording of acoustic signals, such as body sounds or the like, comprising:
transducer means for detecting sound and for producing an input analog signal representative of the sound;
convertor means for receiving the input analog signal from the transducer means and converting the input analog signal to a digital signal;
means coupled to the convertor means for receiving the digital signal and for storing in memory at least a portion of the digital signal;
the convertor means being operable for receiving the digital signal from the memory of the computer means and for converting the digital signal to an output analog signal; and
interface means coupled to the convertor means for receiving the output analog signal and adapted for communicating the output analog signal to the operator.

30. A method of acquiring and processing a sound for assessing a condition, diagnosing a problem, or the like, comprising the steps of:

picking up the sound with a transducer and producing an input analog signal representative of the sound;

converting the input analog signal to a digital signal;

storing at least a portion of the digital signal in non-volatile computer memory;

converting said portion to an output analog signal; and displaying the output analog signal.

* * * * *